US00PP26944P3

(12) United States Plant Patent
Lintott et al.

(10) Patent No.: US PP26,944 P3
(45) Date of Patent: Jul. 12, 2016

(54) ***GAILLARDIA* PLANT NAMED 'SUNSET SNAPPY'**

(50) Latin Name: *Gaillardia×grandiflora*
Varietal Denomination: Sunset Snappy

(71) Applicants: Keith George Lintott, Bognor Regis (GB); Charles Richard Read, Bognor Regis (GB)

(72) Inventors: Keith George Lintott, Bognor Regis (GB); Charles Richard Read, Bognor Regis (GB)

( * ) Notice: Subject to any disclaimer, the term of this patent is extended or adjusted under 35 U.S.C. 154(b) by 78 days.

(21) Appl. No.: 14/544,085

(22) Filed: Nov. 21, 2014

(65) Prior Publication Data

US 2015/0150180 P1 May 28, 2015

Related U.S. Application Data

(60) Provisional application No. 61/963,168, filed on Nov. 25, 2013.

(51) Int. Cl.
*A01H 5/02* (2006.01)

(52) U.S. Cl.
USPC ..... Plt./431

(58) Field of Classification Search
USPC ..... Plt./431
See application file for complete search history.

*Primary Examiner* — Annette Para
(74) *Attorney, Agent, or Firm* — James M. Weatherly; Bethany R. Roahrig; Cochran Freund & Young, LLC

(57) ABSTRACT

A *Gaillardia* plant named 'Sunset Snappy' which is characterized by a long blooming period, compact, low-growing habit and large inflorescences composed of single rows of purple-pink ray florets with cream yellow tips, is disclosed.

2 Drawing Sheets

Figure 1:
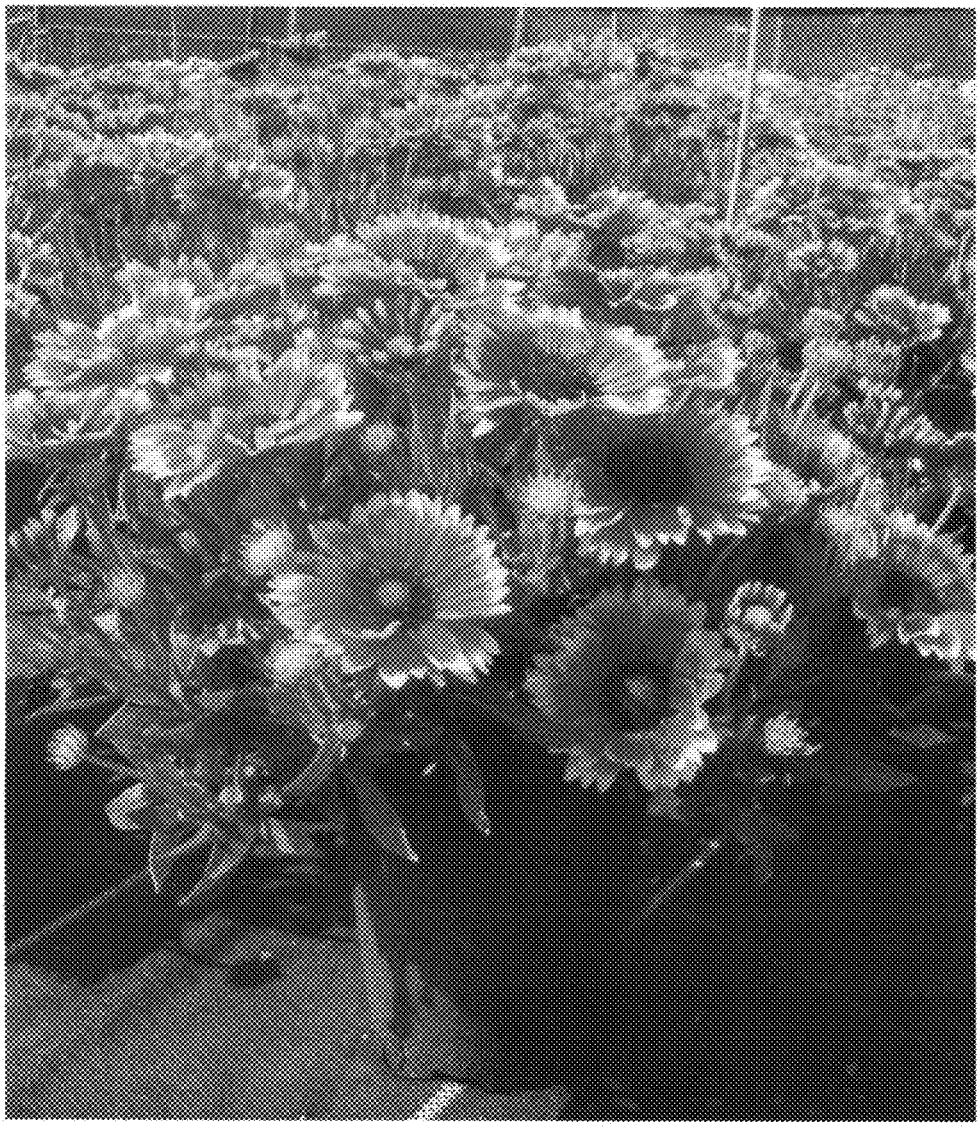

Genus and species: *Gaillardia×grandiflora.*
Denomination: 'Sunset Snappy'.

BACKGROUND

The present disclosure relates to a new and distinct cultivar of blanket flower, an herbaceous perennial that is grown for use as an ornamental landscape and container plant. The plant is known botanically as *Gaillardia×grandiflora* and will be referred to hereinafter by the cultivar name 'Sunset Snappy'. *Gaillardia* is in the family Compositae, under which the commonly referred to "flower" is actually the inflorescence, and made up of smaller ray florets and disc florets. The ray florets themselves have the appearance of "petals".

'Sunset Snappy' originated and was selected from a large population of hybrid seedlings from a *Gaillardia* breeding program, which was started in 2006. The breeding program was conducted in a greenhouse nursery in West Sussex, United Kingdom. The aims of the breeding program are to produce novel combinations of flower colors and flower forms, which are borne on well-branched plants with sturdy growth habits. Controlled hybridization was carried out using combinations of selected named varieties and selected unnamed and unreleased seedlings retained from previous breeding cycles.

'Sunset Snappy' was selected in 2009 for its large flowers, comprised of a single row of purple-pink colored flat ray florets whose tips are cream-yellow in color. Flowers are produced from spring until fall and do not fade with age. 'Sunset Snappy' was also selected for its high bud count and uniform dome-shaped canopy of flowers.

The hybridization which led to the selection of 'Sunset Snappy' was carried out during 2008 using a proprietary unreleased seedling known as 'G722-1' (unpatented) as the male parent and a proprietary unreleased seedling known as 'G716-1' (unpatented) as the female parent.

Sunset Snappy' was first asexually propagated in September 2009 in a greenhouse in West Sussex, United Kingdom using shoot cuttings taken from lateral branches. 'Sunset Snappy' has been found to reproduce true to type in successive generations of asexual propagation.

SUMMARY OF VARIETY 'SUNSET SNAPPY'

The following are the most outstanding and distinguishing characteristics of this new variety when grown under normal horticultural practices in West Sussex, United Kingdom.

1. 'Sunset Snappy' exhibits a compact and naturally branching plant habit;
2. 'Sunset Snappy' exhibits large single inflorescences comprised of a single row or layer of flat ray florets, which are purple-pink in color with cream yellow tips;
3. The disc of 'Sunset Snappy' is deep red in color, with a yellow center, aging to entirely deep red when the inflorescence is fully expanded;
4. 'Sunset Snappy' blooms continually from spring until late fall;
5. 'Sunset Snappy' bears its flowers in a uniform dome-shaped canopy;
6. After one year's growth in a 3 liter container, 'Sunset Snappy' is 35 cm to 40 cm in height and 40 cm to 45 cm in width; and
7. 'Sunset Snappy' is hardy in USDA zone 5.

DESCRIPTION OF THE PHOTOGRAPHS

The accompanying color drawings illustrate the overall appearance of the new *Gaillardia* cultivar 'Sunset Snappy' showing the colors as true as is reasonably possible to obtain in colored reproductions of this type. Colors in the photographs may differ from the color values cited in the detailed botanical description, which more accurately describes the actual colors of the new variety 'Sunset Snappy'.

The drawing labeled as FIG. 1 depicts a whole plant of 'Sunset Snappy', which has been grown in a frost-free greenhouse in West Sussex, United Kingdom. The illustrated plant is one year old and has been grown without any pinching or chemical growth regulator.

Figure 2:
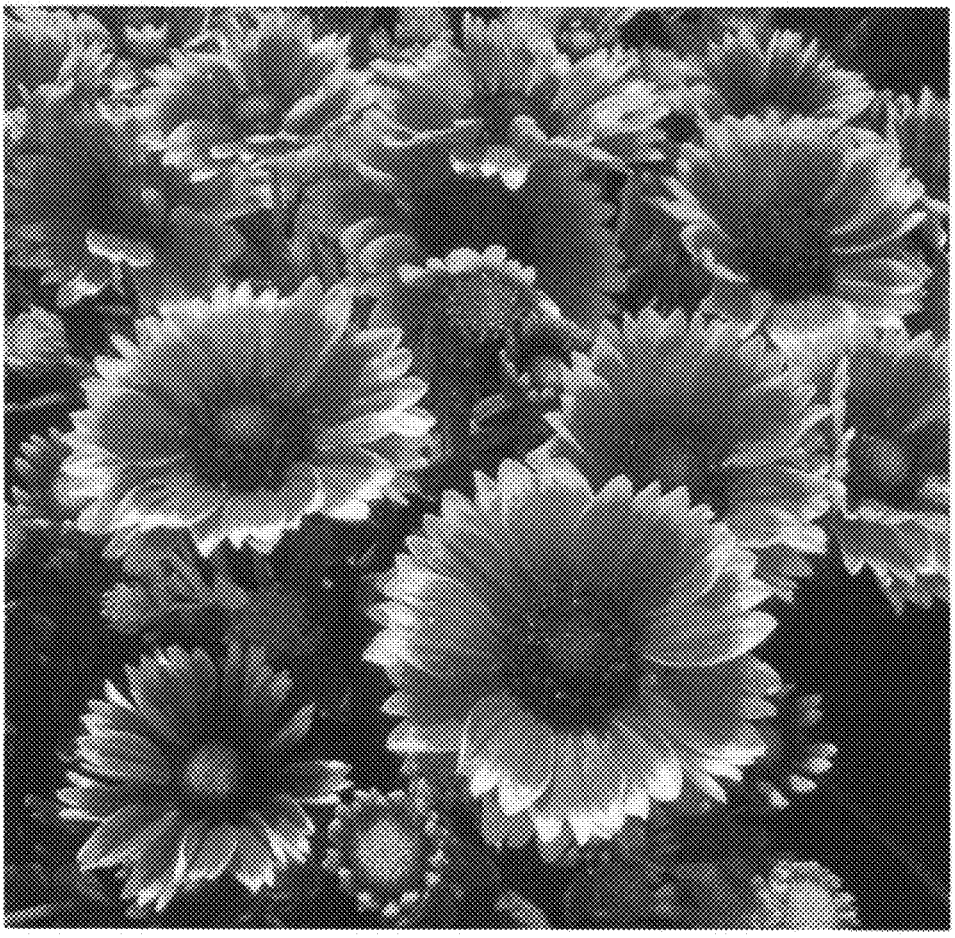

The drawing labeled as FIG. 2 depicts a close up view of the fully expanded inflorescence of 'Sunset Snappy'.

DESCRIPTION OF THE NEW VARIETY

The following is a detailed botanical description of the new *Gaillardia×grandiflora* cultivar 'Sunset Snappy'. Observations, measurements, values and comparisons were compiled during August of 2014 in Santa Barbara, Calif. from a one year old plant growing out of doors in full sun in freely drained proprietary peat-based potting soil. Color determinations are made in accordance with the 2007 edition of The Royal Horticultural Society Colour Chart from London, England, except where general color terms of ordinary dictionary significance are used.

Classification:

*Family.*—Compositae.

*Genus.*—*Gaillardia.*

*Species.*—*×grandiflora.*

*Common name.*—Blanket flower.

Parentage:

*Female parent.*—An unreleased seedling, code number 'G716-1'. (Unpatented).

*Male parent.*—An unreleased seedling, code number 'G722-1'. (Unpatented).

Plant description:

*Propagation method.*—Typically by softwood cuttings although root cuttings have also been successful.

*Rooting system.*—Fine and fibrous.

*Vigor.*—Moderate vigor.

*Time to develop roots.*—14 to 20 days are needed for an initial cutting to develop roots.

*Temperature to develop roots.*—The recommended air temperature is 20 to 21° Centigrade.

*Crop time.*—Approximately 10 weeks to 2 months are needed to produce a 15-centimeter container from a rooted cutting.

*Growth habit.*—Compact and naturally freely branching.

*Suggested container size.*—15-centimeter container.

*Use.*—Ornamental for use as a landscape plant or container plant.

*Type.*—Herbaceous perennial.

*Overall dimensions.*—After one year's growth in a 3 liter container: 35 cm to 40 cm in height and 40 cm to 45 cm in width. At maturity in the ground: 40 cm to 45 cm in height and 50 cm to 55 cm in width.

*Cultural requirements.*—Grow in full sun with moderate water, and well-draining soil such as loam.

*Hardiness.*—USDA Zone 5.

*Special or recommended growing requirements.*—If grown outside in regions which experience winter freezing, 'Sunset Snappy' may be started as a cutting during the spring or summer of the previous year, planted out prior to the onset of winter, and flowering will commence typically in May or June according to the region and season. When grown outside in frost-free regions, or in frost-protected greenhouses, 'Sunset Snappy' will flower virtually all year round and may be started as a cutting (which should be non-flowering) at any time of year.

Stem:

*Branching habit.*—Basal branching.

*Stem color.*—138B.

*Stem dimensions.*—10 cm to 15 cm in length and 5 mm in width.

*Stem shape.*—Cylindrical, slightly fluted longitudinally.

*Stem surface.*—Markedly villous with dense coverage of very fine silvery hairs, approximately 3 mm to 4 mm in length.

*Internode length.*—Average internode length is 10 mm to 12 mm.

Foliage:

*Type.*—Evergreen.

*Leaf arrangement.*—Alternate.

*Margin.*—Entire.

*Leaf shape.*—Oblanceolate.

*Leaf dimensions* (*base of plant*).—20 cm to 23 cm in length, 3.5 cm in width.

*Leaf dimensions* (*at inflorescence height*).—8 cm to 9 cm in length, 2 cm in width.

*Leaf base.*—Truncate.

*Leaf apex.*—Sub-acute.

*Leaf attachment.*—Sessile.

*Leaf color* (*both surfaces*).—138B.

*Leaf venation pattern.*—Parallel. Mid vein protrudes on both surfaces.

*Vein color* (*both surfaces*).—138C.

*Leaf surface* (*both surfaces*).—Pubescent, very fine silvery hairs, lighter than 156D, approximately 0.5 mm to 2.0 mm in length.

*Fragrance.*—A slight sage-like scent when bruised.

Inflorescence:

*Inflorescence.*—Solitary.

*Aspect.*—Facing upward.

*Dimensions of inflorescence.*—85 mm in diameter and 15 mm in height.

*Inflorescence type.*—Radiate capitate with central disc.

*Disc diameter* (*inflorescence fully expanded*).—27 mm to 30 mm.

*Inflorescence number per plant.*—A one-year old plant bears approximately 25 to 30 inflorescences in bud and flower at one time.

*Blooming season.*—From spring until late fall.

*Lastingness of inflorescence.*—8 days, reducing to 6 days in full sun in mid-summer.

Peduncle:

*Peduncle dimensions.*—8 cm to 11 cm in length and 2.5 mm in diameter.

*Peduncle shape.*—Cylindrical.

*Peduncle surface.*—Surface is pubescent and exhibits longitudinal ridges.

*Peduncle color.*—138C.

*Peduncle strength.*—Stiff.

Bud:

*Bud shape.*—Rotate whorl.

*Bud dimensions* (*bud*).—15 mm in diameter and 8 cm in length.

*Bud color.*—138C.

*Bud surface.*—Villous.

Ray florets:

*Ray floret shape.*—Fan shaped with 3 fused petals appearing as lobes.

*Ray floret surface* (*abaxial surface*).—Pubescent.
*Ray floret surface* (*adaxial surface*).—Glabrous.
*Ray floret color* (*abaxial surface*).—180B extending 20 mm to 22 mm from petal base; 12B extending 13 mm from petal (lobe) apex.
*Ray floret color* (*adaxial surface*).—42A extending 20 mm to 22 mm from petal base; 13A extending 13 mm from petal (lobe) apex.
*Ray floret arrangement.*—Radiate.
*Number of ray florets per inflorescence.*—15 ray florets per inflorescence.
*Number of petals per ray floret.*—Three.
*Fused or unfused.*—Petals are basally fused.
*Petal margins of ray florets.*—Entire.
*Ray floret dimensions.*—33 mm to 35 mm in length including the corolla tube, 22 mm in width at the widest point.
*Corolla tube dimensions.*—5 mm in depth and 1.0 mm in diameter.
*Ray floret veins* (*both surfaces*).—Longitudinal, parallel, fine but prominent; color N34A.
*Self-cleaning or persistent.*—Self-cleaning.

Disc florets:
*Quantity of disc florets per inflorescence.*—Numerous, approximately 200 to 250.
*Disc floret dimensions* (*including pistil length*).—9 mm in length and 2.5 mm in width.
*Depth of disc floret corolla tube.*—6 mm in depth.
*Surface of disc florets.*—Lanate.
*Color of disc florets* (*inflorescence newly opening, both surfaces*).—12A.
*Color of disc florets* (*inflorescence fully expanded, both surfaces*).—N34A.
*Phyllary dimensions.*—5.50 cm in diameter and 3 cm in length.
*Phyllary color.*—147B.
*Phyllary arrangement.*—Whorl.
*Number of involucral bracts.*—An average of 25 in number per inflorescence.
*Shape of involucral bract.*—Oblanceolate.
*Involucral bract dimensions.*—2 cm in length and 0.50 cm in width.
*Involucral bract margin.*—Entire.
*Involucral bract apex.*—Acute.
*Involucral bract base.*—Truncate.
*Involucral bract color* (*both surfaces*).—138B.
*Involucral bract surface* (*abaxial surface*).—Pubescent.
*Involucral bract surface* (*adaxial surface*).—Pubescent.
*Fragrance of inflorescence.*—Sweet fragrance.

Reproductive organs:
*Stamens* (*present on disc florets only*).—Three in number, adnate to inner surface of corolla tube.
*Stamen dimensions.*—0.20 mm in width and 5 mm in length.
*Stamen color.*—17A.
*Stamen form.*—Plumose.
*Anther dimensions.*—0.50 mm in length and 1 mm in width.
*Anther color.*—187A.
*Anther shape.*—Narrow lanceolate.
*Pollen.*—Present.
*Quantity of pollen.*—Large amount.
*Pollen color.*—17C.
*Pistil* (*present on ray florets and disc florets*).—One per floret.
*Pistil length.*—12 mm in length.
*Style dimensions.*—2 mm in length and 1 mm in width.
*Style color.*—150D.
*Stigma dimensions.*—8 mm in length and 1.75 mm in width.
*Stigma form.*—Plumose.
*Stigma color.*—187A.
*Stigma shape.*—Bifurcate.
*Ovary position.*—Inferior.
*Ovary color.*—150D.
*Ovary shape.*—Globose.
*Ovary dimensions.*—1 mm in width and 2 mm in height.

Seed:
*Number of seeds.*—Small to moderate amount (ranges from 50 to 100 seeds per inflorescence).
*Seed dimensions.*—5 mm to 6 mm in length (including hairs at apex) and 1 mm to 2 mm in diameter.
*Seed color.*—200A.
*Seed shape.*—Conical with rounded base and apex.
*Seed surface*—Smooth except at apex where many very fine silver hairs, up to 2 mm in length, are present in circular groups.

Resistance to pests and diseases: 'Sunset Snappy' has not been observed to exhibit any resistance to any particular pest or disease. 'Sunset Snappy' is susceptible to downy mildew and to thrips as may be typical of *Gaillardia*.

COMPARISON WITH PARENTAL LINES AND KNOWN VARIETY

'Sunset Snappy' is distinguishable from the female parent, 'G716-1' as follows: The flowers of 'Sunset Snappy' are composed of purple-pink flat ray florets with cream-yellow tips, whereas the female parent bears orange ray florets. 'Sunset Snappy' exhibits a more compact growth habit and darker green foliage than the female parent.

'Sunset Snappy' is distinguishable from the male parent, 'G722-1' as follows: The flowers of 'Sunset Snappy' are more colorfast and age better than the male parent. While 'Sunset Snappy' flowers are borne on strong stems, the male parent exhibits thinner stems and less foliage than the male parent.

The variety of *Gaillardia* which is considered to most closely resemble 'Sunset Snappy' is the variety *Gaillardia* 'Sunset Flash' (U.S. Plant Patent Application to be filed). Whereas the flowers of 'Sunset Flash' are comprised of two rows (layers) of ray florets, which are predominantly orange-red in color, the flowers of 'Sunset Snappy' are comprised of a single row of ray florets which are predominantly purple-pink in color.

'Sunset Snappy' may also be compared with the variety, *Gaillardia* 'Oranges and Lemons' (U.S. Plant Pat. No. 17,092) which is similarly hardy. The flowers of 'Oranges and Lemons' are orange and yellow in color whereas the flowers of 'Sunset Snappy' are purple-pink in color with cream-yellow tips. Additionally, the flowers of 'Sunset Snappy' are larger and more abundant than those of 'Oranges and Lemons'. The plant habit of 'Sunset Snappy' is more compact than that of 'Oranges and Lemons'.

We claim:

1. A new and distinct cultivar of *Gaillardia* plant named 'Sunset Snappy' as described and illustrated herein.

* * * * *